United States Patent [19]

Kruger

[11] Patent Number: 4,743,232
[45] Date of Patent: May 10, 1988

[54] PACKAGE ASSEMBLY FOR PLASTIC FILM BANDAGE

[75] Inventor: Robert J. Kruger, Arlington Heights, Ill.

[73] Assignee: The Clinipad Corporation, Guilford, Conn.

[21] Appl. No.: 915,564

[22] Filed: Oct. 6, 1986

[51] Int. Cl.$^4$ ............................................. A61M 25/02
[52] U.S. Cl. ........................... 604/180; 128/DIG. 26; 128/156; 604/304; 604/307; 206/441
[58] Field of Search ................ 604/180, 177, 174, 263, 604/304, 305, 307, 313, 344; 128/132 R, 132 D, 133, DIG. 26, 156, 169, 171; 206/339, 344, 439–441, 460, 484, 484.1

[56] References Cited

U.S. PATENT DOCUMENTS

| | | |
|---|---|---|
| Re. 31,886 | 5/1985 | Hodgson . |
| Re. 31,887 | 5/1985 | Hodgson . |
| D. 265,423 | 7/1982 | Abraham et al. . |
| 2,344,021 | 3/1944 | Bouziane . |
| 2,721,550 | 10/1955 | Banff ................................ 206/441 |
| 3,007,571 | 11/1961 | Marinaro ......................... 206/441 |
| 3,026,874 | 3/1962 | Stevens . |
| 3,053,255 | 9/1962 | Meyer . |
| 3,064,648 | 11/1962 | Bujan ............................... 604/177 |
| 3,072,249 | 1/1963 | Tritsch ............................. 206/441 |
| 3,089,492 | 5/1963 | Owens . |
| 3,367,332 | 2/1968 | Groves ............................. 604/305 |
| 3,580,254 | 5/1971 | Stewart . |
| 3,610,238 | 10/1971 | Rich, Jr. . |
| 3,782,377 | 1/1974 | Rychlik ............................ 604/180 |
| 4,127,339 | 11/1978 | Malacheski et al. . |
| 4,250,882 | 2/1981 | Adair . |
| 4,297,995 | 11/1981 | Golub . |
| 4,333,468 | 6/1982 | Geist . |
| 4,341,208 | 7/1982 | Gordon . |
| 4,372,303 | 2/1983 | Grossmann et al. . |
| 4,382,441 | 5/1983 | Svedman . |
| 4,513,739 | 4/1985 | Johns . |
| 4,540,412 | 9/1985 | Van Overloop . |
| 4,559,938 | 12/1985 | Metcalfe . |
| 4,627,842 | 12/1986 | Katz ................................. 604/180 |

FOREIGN PATENT DOCUMENTS 1187365  5/1985  Canada ........................... 128/132 D

OTHER PUBLICATIONS

Vincent Falanga, M.D. et al. entitled A Therapeutic Approach to Venous Ulcers; J. Am. Acad, Dermatol., 14:777–784, (1986).

Joseph C. Alper, M.D. et al. entitled Moist Wound Healing Under a Vapor Permeable Membrane, J. Am. Acad. Dermatol., vol. 8, No. 3, Mar., 1983, pp. 347–353.

Joseph C. Alper, M.D. et al. entitled Use of the Vapor Permeable Membrane for Cutaneous Ulcers: Details of Application and Side Effects, J. Am Acad. Dermatol., 11:858–866, (1984).

(List continued on next page.)

Primary Examiner—Dalton L. Truluck
Assistant Examiner—Frank Wilkens
Attorney, Agent, or Firm—Garrettson Ellis

[57] ABSTRACT

A package assembly for a plastic film bandage includes a plastic film bandage having skin adhesive on one side thereof, with a support sheet removably attached to the other side of the bandage and extending beyond the edge of the bandage in at least one area. A tube typically communicates across an end of the bandage with a portion of the tube being positioned against the one side thereof. Means are provided for anchoring the tube into the above-described position. Peel-away protection sheet means are releasably attached to the bandage, covering the one side of the bandage and that portion of the tube which is positioned against the one side. Hinge means are provided, attaching the support sheet and at least a portion of said peel-away protection sheet means at a peripheral position spaced from the bandage. Thus, upon opening, at least a portion of the protection sheet means may be removed from the bandage and may serve as a grippable extension of the support sheet as the bandage is applied to a patient.

10 Claims, 1 Drawing Sheet

OTHER PUBLICATIONS

Joseph C. Alter, M.D. et al. entitled The In Vitro Response of Fibroblasts to the Fluid That Accumulates Under a Vapor—Permeable Membrane, The Journal of Investigative Dermatology, 84:513–515, 1985.

Marla C. Angermeier, M.D. et al. entitled Vapor—Permeable Membrane Theraph for Ulcers of Osteomyelitis, J. Dermatol. Surg. Oncol., 10:5, May 1984, pp. 384–388.

Mathew C. Varghese, M.D. et al. entitled Local Environment of Chronic Wounds Under Synthetic Dressings Arch Dermatol—vol. 122, Jan. 1986, pp. 52–57.

William H. Eaglstein, M.D. entitled Experiences with Biosynthetic Dressings, J. Am. Acad. Dermatol., 12:434–440, 1985.

Friedman & Su entitled Management of Leg Ulcers With Hydrocolloid Occlusive Dressing, Arch Dermatol—vol. 120, Oct. 1984, pp. 1329–1336.

Stepher J. Friedman, M.D. Letter re: Treatment of Dermabrasion Wounds With a Hydrocolloid Occlusive Dressing, Arch Dermatol., vol. 121, Dec. 1985.

Stuart Katz, M.D. et al. entitled Semipermeable Occlusive Dressings Arch Dermatol—vol. 122, Jan. 1986, pp. 58–62.

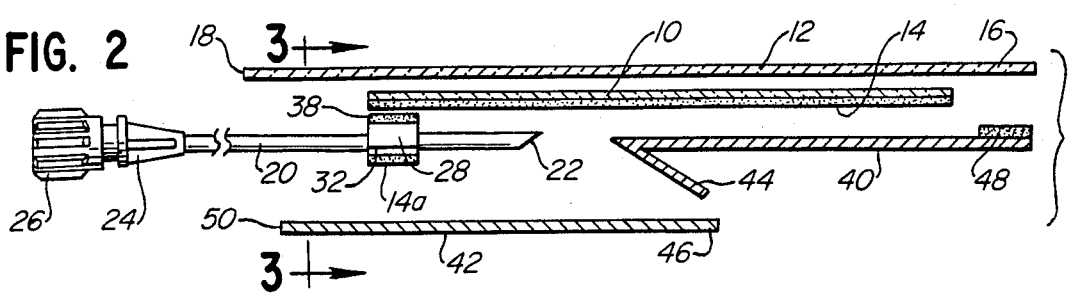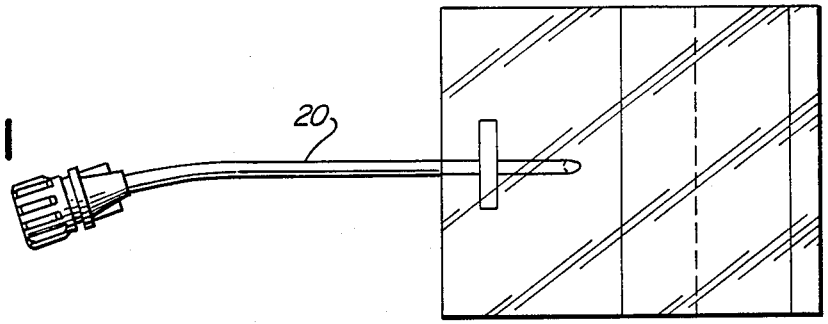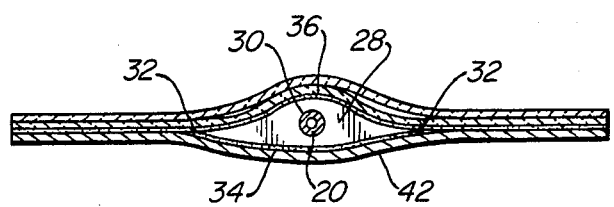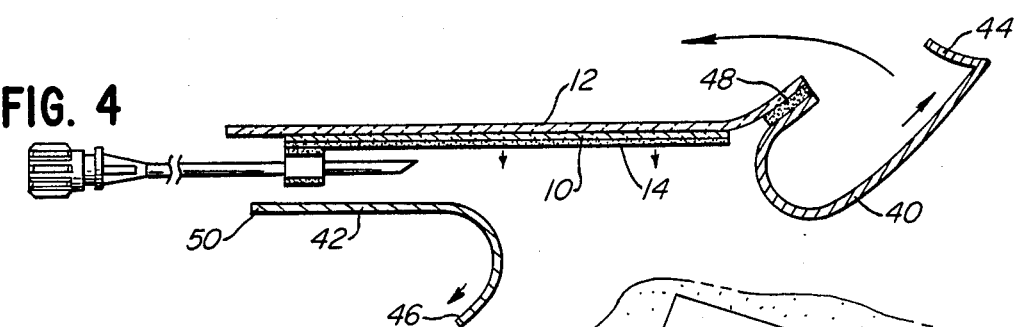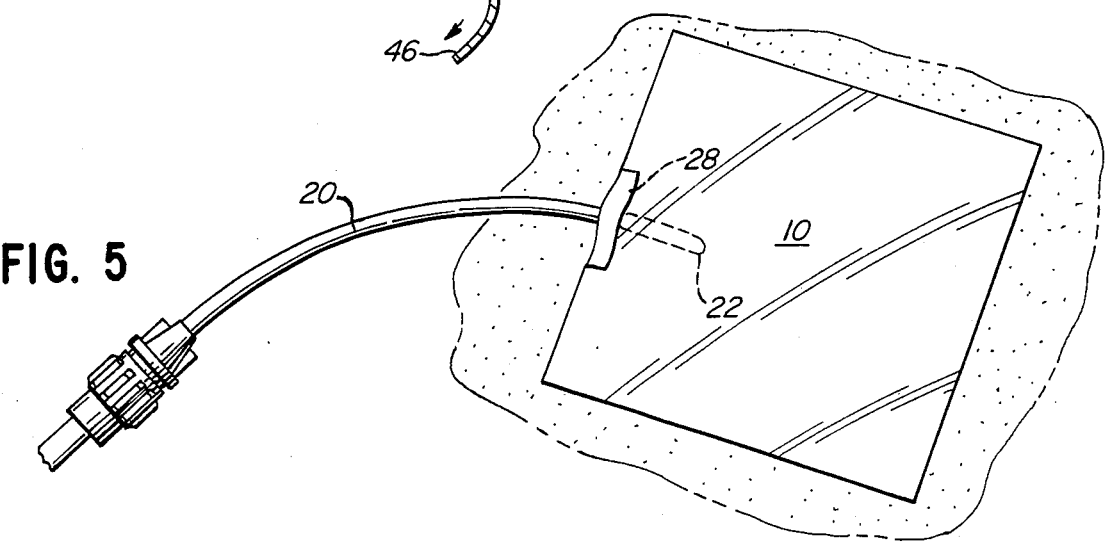

PACKAGE ASSEMBLY FOR PLASTIC FILM BANDAGE

BACKGROUND OF THE INVENTION

There is a growing area of work in the medical field of providing products and processes for establishing a sterile area of skin, where the possibility of irrigation and drainage into and out of the sterile area is provided. See for example Groves U.S. Pat. No. 3,367,332; Adair U.S. Pat. No. 4,250,882; Stevens U.S. Pat. No. 3,026,874; Svedman U.S. Pat. No. 4,382,441; and other, similar patents.

Particularly, bandages for the treatment of chronic skin ulcers are currently on sale, being made of plastic material which is permeable to moisture vapor, but impermeable to liquid aqueous solutions see for example Hodgson U.S. Reissue Pat. Nos. Re. 31,886 and Re. 31,887. Material of this sort from various manufacturers have been used to attempt to permit moist wound healing, either through lavage of the wound by a connecting tube extending through the dressing into a wound site, or by sealing the wound site with a dressing which is liquid impermeable as shown in the article by Vincent Falanga, M.D. et al. entitled A Therapeutic Approach to Venous Ulcers; J. Am. Acad. Dermatol. 14:777–784, (1986). See particularly page 781 of that article. See also the article of Joseph C. Alper, M.D. et al. entitled Moist Wound Healing Under a Vapor Permeable Membrane, J. Am. Acad. Dermatol., Volume 8, Number 3, March, 1983 pages 347–353. Other publications directed to the same subject matter are available as well.

To successfully and efficiently accomplish the various methods of ulcer and wound therapy which involve a plastic film bandage, an effective package assembly for delivering the plastic film bandage into adhered position on the patient, in aseptic condition, is important. As one disadvantage of plastic film bandages which are gas permeable, they tend to be very thin, and not self-supporting. Thus, they wrinkle easily, and generally should be supported by some means to remain flat and unwrinkled until applied on to the desired site of use.

In one available design of plastic film bandage, it is supported by a frame positioned about its periphery, plus a peel-away center portion, to support the bandage in flat configuration until application to its site of use. The opaque, peel-away center portion must be removed to provide the frame structure with an open center so that one may look through the bandage, which is typically at least partially transparent, to view the wound during application thereof to its site of use.

As another problem, virtually every bandage carries peel-away protection sheet means on their adhesive side. In the circumstances in which plastic film bandages are often used, the maintenance of aseptic conditions is very critical. It is important that as the peel-away protection sheet means are removed, there will be no touch contamination of the bandage, particularly its underside.

In accordance with this invention, a package assembly for a plastic film bandage provides improved support and protection of the bandage. Wrinkling of the fragile, non-self-supporting bandage is prevented, and better overall protection is provided to the plastic film bandage until removed from the package. Additionally, manufacturing advantages may be obtained by the invention of this application. Furthermore, an enlarged, grippable extension to the support sheet is provided upon opening, which permits easier application of the bandage to its site of use with less risk of touch contamination.

DESCRIPTION OF THE INVENTION

In this invention, a package assembly for a plastic film bandage comprises such plastic film bandage having skin adhesive on one side thereof. A typically transparent support sheet is removably attached to the other side of said plastic film bandage, the support sheet extending beyond the edge of the bandage in at least one area. Typically, tube communicates across an edge of the bandage, a portion of the tube being positioned against the one bandage side which carries the skin adhesive. Means are provided for anchoring the tube into the above-described position.

Peel-away protection sheet means are releasably attached to the bandage, such protection sheet means covering the one side of the bandage and that portion of the tube which is positioned adjacent the one side. Hinge means attach the support sheet and at least a portion of the peel-away protection sheet means at a peripheral position spaced from the bandage.

As the result of this, upon opening of the package assembly, at least a portion of the protection sheet means may be removed from its connection with the one side of the bandage and may serve as a grippable extension of the support sheet as the bandage is applied to a patient. By means of this, the opened package provides a large, easily grasped backing portion so that the bandage may be manipulated and applied to its site of use with less risk of being touched by the fingers, which can result in touch contamination. At the same time, the support sheet supports the bandage in a flat configuration, preventing the formation of wrinkles, until the bandage is applied to its site of use, following which the support sheet is peeled away from the bandage.

The hinge means described above may be a line of any appropriate adhesive which joins the support sheet and protection sheet means, typically on a permanent basis.

The support sheet and peel-away protection sheet means typically extend beyond the bandage in at least two opposed areas, or, alternatively, the support sheet and protection sheet means may extend beyond the bandage about its entire periphery. This facilitates the manipulation of the bandage during its application to its site of use. One may grasp the peel paper or support sheet with both hands at portions which are spaced from the bandage, after opening, to apply the bandage to the desired place of use.

Typically, the peel-away protection sheet means comprises a pair of separate sheets, one of which is attached to the hinge means described above. However, a single protection sheet may be used. Apart from the attachment to the hinge means, the peel-away protection sheet means may be of a conventional design.

The tube anchoring means may comprise a plastic member defining a tube-receiving bore and a pair of opposed, thin edges positioned essentially parallel to the bore. One wall of the plastic member extends between the edges and is substantially planar, while an opposed wall to the one wall extends between the same edges and defines an outwardly projecting, curved surface. This opposed wall is attached to the adhesive-carrying one side of the bandage by means either of some of the skin adhesive on the bandage, or by another adhesive, as desired. Such a design of tube anchoring means may provide good sealing of its section of the periphery of the bandage so liquids in the wound or ulcer cannot easily leak out through the peripheral area. Typically, the bandage is coated about at least its periphery with the skin adhesive so that a good peripheral seal exists.

Other types of tube anchoring means which provide sealing may be utilized if desired.

The support sheet is preferably made of a transparent material so that the site to which the bandage is being applied may be seen through both the support sheet and the bandage, which is also preferably transparent to at least a certain extent, to permit this to take place. Thus, the support sheet of this invention does not have to have a cut away center, as in the prior art, for visualization of the site of application of the bandage.

DESCRIPTION OF THE DRAWINGS

FIG. 1 is a plan view of the package assembly of this invention, containing a bandage;

FIG. 2 is an exploded elevational view of the package assembly of FIG. 1;

FIG. 3 is a sectional view taken along line 3—3 of FIG. 2, but not shown in exploded relation;

FIG. 4 is an elevational view of the system of the previous drawings shown in an opened configuration as the bandage is being applied to its site of use; and FIG. 5 is a perspective view of the bandage as positioned at its site of use.

DESCRIPTION OF SPECIFIC EMBODIMENT

Referring to the drawings, a plastic film bandage 10 is provided for covering ulcers or other wounds. Preferably, the plastic film is capable of preventing migration of liquids from the ulcer or other wound, while providing adequate transfer of gases therethrough for tissue health, being microporous in nature and of a type known to those skilled in the art. One type of plastic film that may be used is covered in U.S. Reissue Pat. Nos. 31,886 and 31,887. However, an alternate and preferred type of material is commercially available from the Fasson Industrial Division of Avery International, Plainsville, Ohio. This material is a polyether-polyamide copolymer elastomer. One particularly desirable grade is sold under the name Medifilm 810, being provided as a very thin film, carried on a casting sheet of polypropylene, which may serve as support sheet 12 for purposes of this invention. Such polyether-polyamide copolymer elastomers can have significantly improved water vapor transmission rates which provide reduced skin irritation and better wound healing.

Plastic film bandage 10 may then carry, on its first side opposed to support sheet 12, a film of skin adhesive 14, for example an acrylic adhesive such as Fasson I-679 with a thickness of about 0.002 inch. The thickness of plastic film bandage 10 is preferably about 0.0005 to 0.002 inch thick.

It can be seen that support sheet 12 extends beyond bandage 10 at two opposed regions 16, 18. This permits grasping of the package assembly at the two ends 16, 18, without touch contamination of film bandage 10, to preserve sterility.

In this particular embodiment, a tube 20, typically made of polyvinyl chloride, communicates across an edge of bandage 10 as shown so that one, typically tapered, end 22 of tube 20 communicates with the first side of bandage 10, and the other end of tube 20 communicates with the exterior. A luer adaptor 24 and cap 26 of conventional design, may be carried by tube 20 at its outer end, and as shown.

Tube 20 passes through a resilient plastic member 28 which defines a tube-receiving bore 30 and a pair of opposed, thin edges 32, positioned essentially parallel to bore 30. One wall 34 of said plastic member 28, extending between edges 32, is typically substantially planar, while an opposed wall 36 thereto, extending between edges 32, defines an outwardly projecting, curved surface. Opposed wall 36 is attached to the one face of film bandage 10 by a strong adhesive, generally a permanent adhesive, e.g., a permanent acrylic adhesive. Generally planar wall 34 of plastic member 28 may be coated with the same skin adhesive 14a as covers the first side of bandage 10. The adhesive coating 14 of bandage 10 may be continuous or discontinuous, as may be desired, but generally with the objective of preventing the seepage of liquids from the center of the bandage outwardly across the periphery thereof, while the bandage is mounted on the skin. Accordingly, a foamed adhesive may be used having micro-discontinuities, although it is generally preferred that at least the peripheral area of adhesive 14 (and 14a) be sufficiently solid to prevent such liquid migration. Instead, in embodiments where tube 20 is used, liquids under bandage 10 may be drained through the tube, and the ulcer or wound site enclosed by the bandage may be flushed with flushing solutions, if desired.

Alternatively, the package assembly of this application may be provided without tube 20 and plastic member 28, to provide a simple, flat bandage. If desired, tube 20 may be replaced by an electrical lead or other elongated member for other therapeutic or monitoring purposes.

In this particular embodiment, a pair of peel-away protection sheets 40, 42 may be provided, which adhere to skin adhesive layers 14, 14a, and may be peeled away in the entirely conventional manner of bandage technology. As shown, protection sheet 40 has a folded portion 44 in conventional manner over which inner end 46 of sheet 42 overlies, for finger gripping purposes to open the device of this invention.

A line of typically permanent adhesive 48 is provided to join support sheet 12 with peel-away protection sheet 40, to define a hinge. Hinge 48 is typically spaced from bandage 10, as shown, and communicates with the outwardly extending end 16 of support sheet 12. The outer end 50 of peel-away protection sheet 42 is shown to extend outwardly beyond film bandage 10 in the other direction to an extent approximating the outwardly extending end portion 18 of support sheet 12.

The package assembly of this invention may be easily assembled by automated processing machinery at a very low cost and with high reliability. The package assembly may be sterilized with ethylene oxide gas, radiation, or any other desired technique. A peripheral seal can be provided around the periphery of bandage 10 between adhesive layers 14 and 14a and protection sheets 40, 42, to maintain the first side of bandage 10 and the adhesive layer 14 carried thereon under sterile conditions until opening of the package.

Referring to FIG. 4, one preferred way of opening the package assembly of this invention for application of bandage 10 to its site of use is first to gras protection sheet 42 at its end 46 (or end 50) and remove it. Then, without touching the exposed adhesive surface 14 of bandage 10, end 18 of support sheet 12 is grasped. With the other hand, one grasps folded end portion 44 of protection sheet 40 to pull it away from bandage 10, stretching support sheet 12 and protection sheet 40 into a more or less planar array, which completely exposes bandage 10, while the hands remain substantially spaced from the bandage. Bandage 10 retains a light adhesion with support sheet 12. This may be done by the use of a light adhesive, or, if bandage 10 has been cast upon support sheet 12 in its original manufacture, such light adhesion may be spontaneously present without the need for an adhesive.

One then is in a position to apply bandage 10 to the site of use on a patient by bringing the combined, grasped support sheet 12 and protection sheet 40 typically downwardly, until bandage 10 is thoroughly in contact with the skin site upon which it is to reside. This takes place without wrinkling of the bandage because it is carried over its entire area upon support sheet 12. One may then manually rub or press support sheet 12 to cause bandage 10 to enter into good adhesion with the skin.

Following this, one may peel away support sheet 12 from the other side of bandage 10 leaving bandage 10 alone on its skin site as shown in FIG. 5, with tube 20 being anchored in place, having end 22 positioned under bandage 10 so that body fluids may be drained and washing solutions and the like may be added to the area underneath bandage 10 without breaking the sterility barrier provided by the bandage.

Support sheet 12 may preferably be made of polypropylene, polyethylene, polyesters (such as Mylar brand polyester), or the like to provide low but positive adhesion with bandage 10, especially when the plastic of bandage 10 is cast onto sheet 12 during manufacture. Alternatively, polytetrafluoroethylene may be used if less transparency is acceptable.

The above has been offered for illustrative purposes only, and is not intended to limit the scope of the invention of this application, which is as defined in the claims below.

That which is claimed is:

1. A package assembly for a plastic film bandage, which comprises:
   a plastic film bandage having skin adhesive on one side thereof; a support sheet removably attached to the other side opposed to said one side of said plastic film bandage and extending beyond the edge of said bandage in at least one area; a tube communicating across an edge of said bandage, a portion of said tube being positioned against said one side thereof; means for anchoring said tube into the above-described position; peel-away protection sheet means releasably attached to said bandage and covering the one side of said bandage and that portion of said tube which is positioned against said one side; and hinge means attaching said support sheet and at least a portion of said peel-away protection sheet means at a peripheral position spaced from said bandage, whereby upon opening, at least a portion of said protection sheet means may be removed and may serve as a grippable extension of said support sheet as the bandage is applied to a patient.

2. The package assembly of claim 1 in which said hinge means is a line of permanent adhesive which joins said support sheet and protection sheet means.

3. The package assembly of claim 1 in which said tube anchoring means comprises a plastic member defining a tube-receiving bore and a pair of opposed thin edges positioned essentially parallel to said bore, one wall so said plastic members extending between said edges being substantially planar, and an opposed wall thereto extending between said edges defining an outwardly projecting curved surface, said opposed wall being attached to said one side of the bandage.

4. The package assembly of claim 1 in which said peel-away protection sheet means comprises a pair of separate sheets, one of which is attached to said hinge means.

5. The package assembly of claim 1 in which said support sheet is transparent.

6. The package assembly of claim 1 in which said support sheet extends beyond said bandage in at least two, opposed areas.

7. A package assembly for a plastic film bandage, which comprises:
   a plastic film bandage having skin adhesive on one side thereof; a transparent support sheet removably attached to the other side of said plastic film bandage and extending beyond the edge of said bandage in at least one area; a tube communicating across an edge of said bandage, a portion of said tube being positioned against said one side thereof; means for anchoring said tube into the above-described position, said anchoring means comprising a plastic member defining a tube-receiving bore and a pair of opposed, thin edges positioned essentially parallel to said bore, one wall of said plastic member extending between said edges being substantially planar, and an opposed wall of said plastic member extending between said edges defining an outwardly projecting, curved surface, said opposed wall being attached to said on side of the bandage; peel-away protection sheet means releasably attached to said bandage and covering the one side of said bandage and that portion of said tube which is positioned against said one side; and hinge means attaching said support sheet and at least a portion of said peel-away protection sheet means at a peripheral position spaced from said bandage, said hinge means being defined by a line of adhesive which joins said support sheet and protection sheet means, whereby, upon opening of said package assembly, at least a portion of said protection sheet means may be removed from contact with the plastic film bandage and may serve as a grippable extension of said support sheet as the bandage is applied to a patient.

8. The package assembly of claim 7 in which said peel-away protection sheet means comprises a pair of separate sheets, one of which is attached to said hinge means.

9. The method of applying a plastic film bandage having skin adhesive on one side thereof to a patient, said plastic film bandage having a support sheet removably attached to the other side opposed to said one side of said plastic film bandage and extending beyond the edge of said bandage in at least a pair of opposed areas, said bandage carrying a tube which communicates across an edge of said bandage, a portion of said tube being positioned against said one side thereof, said tube having means for anchoring it into position, said bandage plus said anchoring means and a portion of said tube also being covered with peel-away protection sheet means on said one side of the bandage, said support sheet and peel-away protection sheet means being connected together at a peripheral position spaced from said bandage by hinge means, which method comprises:

removing said peel-away protection sheet means from the one side of the bandage to expose said skin adhesive; gripping at least a portion of said protection sheet means to extend it into approximately a plane similar to the plane occupied by said support sheet, with said extended portion of the protection sheet means and support sheet being connected by said hinge means, while grasping an opposed area of said support sheet on the other side of said bandage from said hange means, without touching said bandage;

bringing the adhesive-carrying one side of said bandage into adjacent, facing relation to the site of application without touching said bandage, and bringing said one side into adhesive contact with said site of application; and thereafter peeling away said support sheet from said plastic film bandage.

10. The package assembly of claim 7 in which said hinge means is a line of permanent adhesive.

* * * * *